(12) United States Patent
Kalombo

(10) Patent No.: US 8,518,450 B2
(45) Date of Patent: Aug. 27, 2013

(54) NANOPARTICLE CARRIERS FOR DRUG ADMINISTRATION AND PROCESS FOR PRODUCING SAME

(75) Inventor: Lonji Kalombo, Pretoria (ZA)

(73) Assignee: CSIR, Pretoria (ZA)

( * ) Notice: Subject to any disclaimer, the term of this patent is extended or adjusted under 35 U.S.C. 154(b) by 0 days.

(21) Appl. No.: 12/858,074

(22) Filed: Aug. 17, 2010

(65) Prior Publication Data

US 2011/0033550 A1 Feb. 10, 2011

Related U.S. Application Data

(63) Continuation-in-part of application No. PCT/ZA2008/000012, filed on Feb. 18, 2008.

(51) Int. Cl.
| | |
|---|---|
| *A61K 9/14* | (2006.01) |
| *A61K 31/496* | (2006.01) |
| *A61K 31/4409* | (2006.01) |
| *A61K 31/133* | (2006.01) |
| *A61K 31/4965* | (2006.01) |

(52) U.S. Cl.
USPC ...... 424/499; 424/489; 424/501; 514/254.11; 514/354; 514/669; 514/255.06

(58) Field of Classification Search
USPC ............ 424/499, 489, 501; 514/254, 254.11, 514/354
See application file for complete search history.

(56) References Cited

U.S. PATENT DOCUMENTS

| | | | | |
|---|---|---|---|---|
| 4,652,441 | A * | 3/1987 | Okada et al. | 424/497 |
| 6,419,949 | B1 * | 7/2002 | Gasco | 424/450 |
| 6,632,671 | B2 * | 10/2003 | Unger | 435/455 |
| 6,872,696 | B2 * | 3/2005 | Becker et al. | 510/392 |
| 2004/0018236 | A1 * | 1/2004 | Gurny et al. | 424/471 |
| 2005/0107263 | A1 * | 5/2005 | Bland et al. | 507/203 |
| 2010/0215580 | A1 * | 8/2010 | Hanes et al. | 424/9.1 |

FOREIGN PATENT DOCUMENTS

| | | | |
|---|---|---|---|
| EP | 1595549 | | 11/2005 |
| WO | 03/099262 | | 12/2003 |
| WO | WO 03/099262 | * | 12/2003 |
| WO | WO 2008/026894 | * | 3/2008 |

* cited by examiner

*Primary Examiner* — Anoop Singh
*Assistant Examiner* — Anna Falkowitz
(74) *Attorney, Agent, or Firm* — Occhiuti Rohlicek & Tsao LLP

(57) ABSTRACT

The invention provides a process for the production of nanoparticle carriers for drug delivery, said nanoparticles being produced by preparing a double emulsion of water-oil-water including one or more polymer which forms the basis of the nanoparticle carrier, blending the drug to be delivered into one of the emulsion phases, doping either the oil-phase or the outer-water phase with a carbohydrate, and spray drying the emulsion to form nanoparticles of a narrow particle size distribution of 100 nm to 1000 nm, which nanoparticles are substantially spherical.

22 Claims, 2 Drawing Sheets

NANOPARTICLE CARRIERS FOR DRUG ADMINISTRATION AND PROCESS FOR PRODUCING SAME

CROSS REFERENCE TO RELATED APPLICATION

This application is a continuation-in-part of PCT Application No. PCT/ZA2008/000012, filed on Feb. 18, 2008, the content of which is incorporated herein by reference.

FIELD OF THE INVENTION

The invention relates to nanoparticle carriers for oral administration of medically active compounds and/or other compounds.

BACKGROUND TO THE INVENTION

The spray-drying technique has seen wide application in the preparation of pharmaceutical powders, mostly for pulmonary drug delivery, with specific characteristics such as particle size, density and shape. It is a well-established method for producing solid powder by atomising suspensions or solutions into droplets followed by a drying process in flowing hot air.

Although most often considered as a dehydration process, spray-drying can also be used as an encapsulation method where active substances are entrapped in a polymeric matrix or shell. It is reported that several colloidal systems such as emulsions or liposomes were successfully spray dried with preservation of their structure using drying-aid agents, particularly sugars such as lactose, sorbitol and trehalose.

One of the merits of the spray-drying technique is that it is a cost effective and quick drying process applicable to a broad range of pharmaceutical products and leading to the production of a free flowing powder, characterized by very low water content, preventing therefore the degradation of the active. This is meaningful for the development of long-term stable carriers, mostly when these carriers are in the range of nano scale, designed specifically for the delivery of active compounds at the site of interest.

Recently, it has been shown that the spray drying technique can produce nano scale solid particles and solid lipid nanoparticles loaded with active agents to be used as delivery systems for pulmonary airways. It is worthwhile to note that in most cases where this technique was applied to produce solid nanoparticles, it was, in fact, a drying process of nanocapsules obtained by other techniques. Thereafter the suspension of the nanoparticles was subjected to spray drying. This resulted often in the production of particles with very broad size range from nano to micron size, despite the presence of disaccharides as drying excipients in the formulation.

Recently, it was reported the spray drying of a liquid colloidal system in the drug delivery field, where a single emulsion (water-in-oil emulsion) containing DNA encapsulated in poly(lactic-co-glycolic acid (PLGA), was successfully spray dried. Another report was made on spray drying of a double emulsion (oil-in-water-in-oil or O/W/O), in the presence of lactose, aiming to preserve orange oil and in both cases the particles produced were in the micron size range.

A need has been identified for spherical nanoparticles having a narrow size distribution range, typically from 180 to 250 nm. Ideally such particles should have a substantially smooth surface and be free flowing.

SUMMARY OF THE INVENTION

The invention provides a process for the production of nanoparticle carriers for drug delivery, said nanoparticles being produced by:
preparing a double emulsion of water-oil-water including one or more polymer which forms the basis of the nanoparticle carrier;
blending the drug to be delivered into one or more of the emulsion phases;
doping either the oil-phase or the outer-water phase with a carbohydrate; and
spray drying the emulsion to form nanoparticles of a narrow particle size distribution of 100 nm to 1000 nm.

The nanoparticles thus produced may be multifunctional nanoparticles.

The carbohydrate may be a saccharide.

The saccharide may be a disaccharide.

The disaccharide may be lactose, maltose, isomaltose, mannobiose, trehalose, cellobiose, or the like.

The saccharide may be combined with a cationic biodegradable muco-adhesive polysaccharide.

The polysaccharide may be chitosan or derivatives thereof.

The oil-phase of the emulsion may be doped with a surfactant.

The water-phase of the emulsion may be doped with surfactant.

The outer water-phase of the emulsion may be doped with surfactant.

The surfactant may be a Gemini surfactant.

The surfactant may be a nonionic surfactant.

The surfactant may be based on acetylenic diol chemistry.

Gemini, also called dimeric, surfactants belong to a relatively new class of surfactant molecules that possess more than one hydrophobic tail and hydrophilic head group. These features result in enhanced surface-active properties for gemini surfactants compared to the corresponding monomeric surfactants. They could be anionic, cationic, nonionic or amphoteric. In their structure, gemini's are generally symmetrical compounds characterised by at least two identical hydrophobic chains and two identical ionic or polar groups linked by spacers of various nature. The spacers vary in length, hydrophobicity and flexibility.

For emulsification purposes, the most used nonionic Gemini surfactants belong to the family of acetylenic diol-based ethoxylated dimeric surfactants with the following generic name: $\alpha,\alpha'$-[2,4,7,9-tetramethyl-5-decyne-4,7-diyl]bis[$\omega$-hydroxylpoly(oxyethylene)]. The surface activity of such a molecule is a function of the number of ethylene oxide groups attached on the backbone of the surfactant molecule. They form relatively stable emulsions when added at a very low level as compared to conventional surfactants. For illustration, an ethoxylated Gemini surfactant can reduce water surface tension by more than 50% when added at a concentration as low as 1 mM as opposed to conventional monomeric surfactants that require hundred times higher concentrations to achieve the same effect.

The surfactant may be a polymeric nonionic surfactant.

The polymeric nonionic surfactant in the water-phase may be polyvinyl alcohol (PVA), partially hydrolysed.

The polymer may be in the oil-phase of the emulsion.

The polymer in the oil-phase may be PLGA (poly(lactic-co-glycolic acid)).

Both oil-phase and water-phase polymers may be present.

The drug may be added to the oil-phase.

The drug may be a hydrophilic drug which is added to the internal water-phase.

The drug may be hydrophobic and may optionally be added to the oil phase.

The drug may be Rifampicin, Isoniazid, Ethambutol, or Pyrazynamide.

The outer water-phase of the emulsion may include polyethylene glycol (PEG).

The oil-phase may include stearic acid.

The nanoparticles thus formed may be substantially spherical.

The particle size distribution of the nanoparticles may be from 180 nm to 250 nm diameter.

The description of embodiments which follows should be interpreted broadly and not to limit the scope of the invention.

DETAILED DESCRIPTION

1. Object of Experiment

Figure 1:
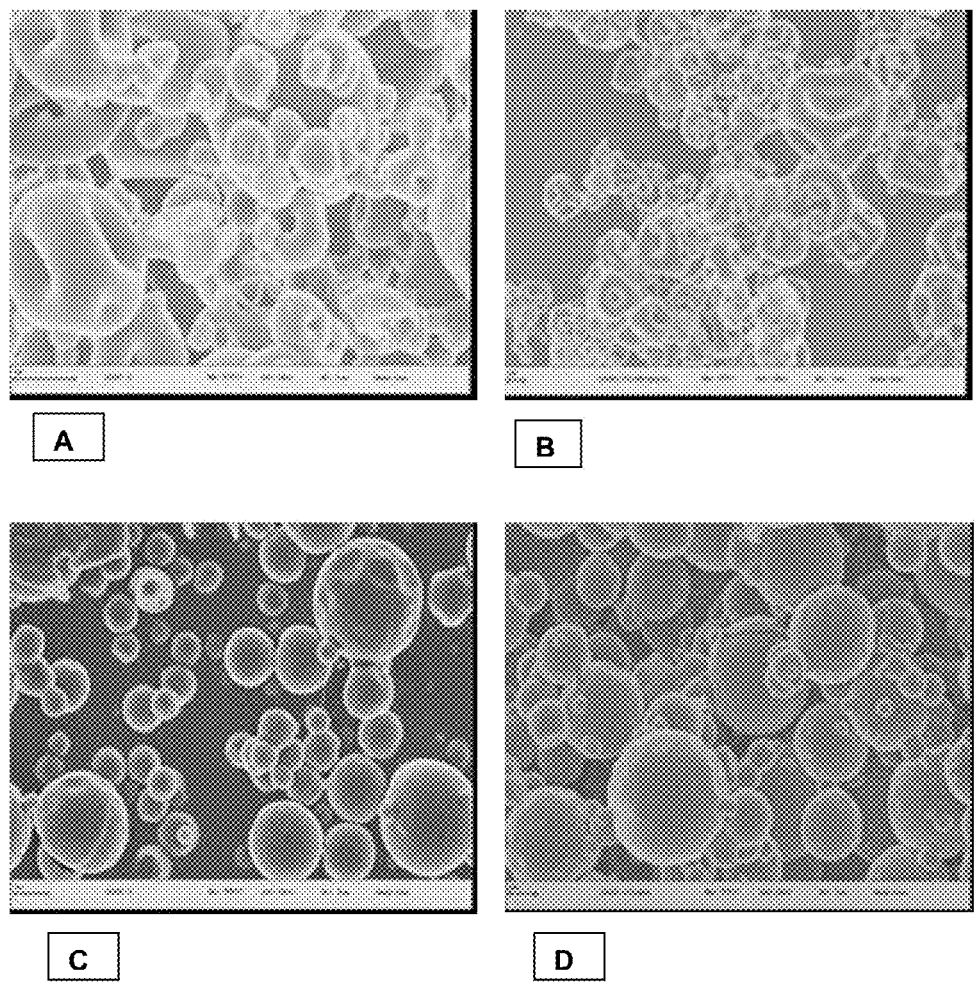
FIGS. 1A-1D are SEM micrographs of INH-loaded PLGA nanoparticles spray dried: A. using DCM; B. using EA; C. DCM+10% (w/v) lactose and D. EA+10% (w/v) lactose.

For this experiment, anti-tuberculosis antibiotics including isoniazid (INH) ethambutol (ETH), pyrazynamide (PZA) and Rifampicin have been successfully loaded in polymeric core-shell nanoparticles of poly DL, lactic-co-glycolic acid (PLGA50:50), a biodegradable and biocompatible polymer, extensively used as a carrier. Submicron solid particles of PLGA incorporating INH (or Eth or PZA or RIF) have been obtained by spray drying straightforward a typical double emulsion water-in-oil-in-water (W/O/W).

In the formulation, chitosan, a cationic biodegradable muco-adhesive polysaccharide, was employed as absorption enhancer while lactose monohydrate was used as spray drying-aid. PVA was considered as the main stabiliser component of the double emulsion, while PEG was incorporated to increase the bio-circulation of the carrier.

Surfynol 104 PG-50™, as a co-surfactant, played a big role in decreasing the particle size towards the nanosize range while significantly narrowing the size distribution.

2. Materials and Methods

2.1 Materials

The frontline anti-tuberculosis drugs were purchased from Sigma. Poly, DL, Lactic-co-Glycolic Acid, (PLGA) 50:50 (Mw: 45000-75000) and chitosan low Mw, 85% de-acetylated, were both supplied by Sigma. Polyvinyl alcohol (PVA) (Mw: 13000-23000 and partially hydrolysed (87-89%) was also obtained from Sigma. Stearic acid supplied by Merck, Surfynol 104 PG-50™, a Gemini diol type surfactant, was supplied by Air Products. Polyethylene glycol (PEG) (Mw 9000) was purchased from BASF Chemicals. Lactose monohydrate supplied by Merck, was used as an excipient.

Dichloromethane, ethyl acetate and acetonitrile, analytical and HPLC grades were also supplied by Merck.

2.2 Methods
2.2.1 Formulation

The preparation of nanoparticles was achieved by the method based on the interfacial polymer precipitation from a double emulsion W/O/W subsequent to the evaporation of the organic solvent. In this invention, the step of solvent evaporation and drying was combined in one step by applying the spray drying technique.

Briefly, 50 mg of INH was dissolved in a 2 ml of phosphate buffer solution (pH7.4), which was added to a solution of 100 mg of PLGA (50:50) dissolved in 8 ml of the organic solvent (DCM or ethyl acetate). An optional 2 ml of 0.2% (w/v) of stearic acid can also be dissolved in the same solvent (DCM or Ethyl acetate). A drop of Surfynol 104 PG-50™ was intentionally added either to the PLGA oil phase or to the external aqueous phase containing PVA.

The mixture was subject to emulsification using the high speed homogeniser (Silverson L4R) at 5000 rpm for 3 min to produce W/O emulsion. This first emulsion obtained was then immediately poured into an aqueous phase volume of a known concentration of PVA (1 or 2% w/v), PEG 0.5% w/v, chitosan and lactose aqueous solution in a defined volume ratio, and emulsified to form the double emulsion W/O/W again by means of the high speed homogenizer (Silverson L4R) at 8000 rpm for 5 min. The final emulsion obtained was directly fed through a spray dryer to produce nanoparticles using the conditions specified in Table 1.

Spray Drying

A Büchi mini spray dryer model B-290 (Büchi Lab, Switzerland) with a standard nozzle (0.7 mm diameter) was used to produce the dry powders of the various formulations. The conditions used are compiled in Table 1:

TABLE 1

| Spray-drying process condition of B-290 Büchi Mini Spray Drier | |
|---|---|
| Condition | Parameter |
| Atomizing air volumetric flow rate | 800 NL/h |
| Feeding rate | 1.0 mL/min |
| Aspirator rate | 100% |
| Inlet (outlet) temperature | 90-110° C. (53-63° C.) |
| Pressure for atomisation | 6-7 bars |

The spray dryer was provided with a high performance cyclone, designed to get an excellent recovery of the material in the receiver vessel and reduce the adhesion of the product on the wall of the drying chamber.

2.2.2 Particle Size and Size Distribution

Particle size and particle size distributions were measured by Dynamic Laser Scattering or Photon Correlation Spectroscopy using a Malvern Zetasizer Nano ZS (Malvern Instruments Ltd, UK). For each sample 3-5 mg of spray dried powder were prepared by suspending the particles in filtered water (0.2 μm filter), vortexing and/or sonicating for 2 min if necessary. Each sample was measured in triplicate.

2.2.3 Zeta Potential

The zeta potential of the particles was measured using the Zetasizer Nano ZS (Malvern Instruments Ltd, UK). For that a sample of 3 mg of the spray dried nanoparticles was suspended in 1-2 ml of de-ionised water and then vortexed or sonicated before the measurement. Each measurement was taken in triplicate.

2.2.4 Scanning Electron Microscope

Surface morphology of spray dried nanoparticles was visualized by scanning electron microscopy (LEO 1525 Field Emission SEM.). A small amount of nanoparticle powder was mounted on a brass stub using a double-sided adhesive tape and vacuum-coated with a thin layer of gold by sputtering.

2.2.5 Drug Incorporation

The amount of the hydrophilic drug Isoniazid that was entrapped in the particle powder after the nanoencapsulation process was measured in triplicate using a spectrophotometric method (UV-Vis, Thermo Spectronic Heliosα). The encapsulation efficiency of INH in nanoparticles was determined as the mass ratio of the entrapped INH to the theoretical amount of INH used in the preparation. For that, 50 mg of precipitated particles were re-suspended in 20 ml of deionised water, centrifuged (10 000 rpm/10 C/5 min) to remove the un-encapsulated drug and the supernatant was subject to UV-Vis Spectrophotometer, read at $\lambda=262$ nm for INH assessment. The encapsulated amount of INH was determined by subtracting INH in the supernatant from total initial INH amount.

INH Stability Assessment Using HPLC

The stability of INH spray dried powders was assessed by reverse phase-high performance liquid chromatography-analysis (RP-HPLC) using Shimadzu machine supplied with Photodiode Array (PDA) detector.

The following characteristics were applied: a Column Phenomenex [(C18 (5 µm); (250×4.6 mm ID)], a mobile phase of 5% (v/v) acetonitrile with 95% (v/v) buffer $NaH_2PO_4$ (pH 6.8), at a flow rate of 1 ml/min and at a temperature of 30° C. The detection was performed using PDA at $\lambda=259$ nm, on a total injection volume of 20 µl.

3. Results and Discussion

All spray drying runs produced nanoparticles with a size ranging from approximately 220 to 800 nm. The concentration of the liquid feed did not show any influence on the size of particles as illustrated with samples where the PVA concentration was changed from 1 to 2%. Only the addition of lactose and Surfynol 104 PG-50™ demonstrated a significant impact on the size and the morphology of nanoparticles. Interestingly, just one drop of the Gemini surfactant added to the oil phase, drastically reduced the size and the size distribution of the product, irrespective of either the type of organic solvent or the concentration of PVA.

During all the sets of experiments beside the temperature, all other parameters of the spray dryer were kept constant. The mass ratio PLGA:INH (2:1) was also unchanged. The addition of lactose improved significantly the shape of nanoparticles. This effect was pronounced when dichloromethane was used as organic solvent.

The yields of the powder for all the formulations investigated were in the range of 40-70%.

The residual water content of selected samples, determined by thermal analysis, showed a very low level of moisture (~3%).

Results obtained from HPLC indicated the degradation of INH, possibly due to interaction with lactose. This challenge was overcome by capping the functional group The encapsulation efficiency of INH is approximating 60%.

3.1 Effect of Solvent on Particles Size and Morphology

The most commonly used organic solvents in double emulsion technique are dichloromethane (DCM) and ethyl acetate (EA).

Thus, we decided to monitor the size and the morphology of nanoparticles by varying the organic solvent. In all cases, when ethyl acetate was used as organic solvent, the first emulsion obtained presented an aspect of a transient stable emulsion, this observation being based on the less milky appearance of the emulsion when compared to the one obtained with DCM.

EA samples produced very irregular surface morphology compared to samples prepared with DCM. Particles from EA were highly dimpled and wrinkled before addition of lactose. Small doughnut-shaped particles were also observed

3.2 Effect of Additives

3.2.1 Effect of Lactose on Particle Size and Morphology

The size and the shape as well as surface morphology of nanoparticles were strongly affected by the composition of the phases. As the initial concentration of lactose was increased from 5 to 10% w/v, the particles shifted from highly wrinkled to nearly smooth spheres. The fraction of doughnut-shaped particles decreased sensibly, regardless the type of solvent used, as depicted by SEM pictures in FIGS. 1C and D. However, much more surface smoothness has been observed with DCM in the scale of observation.

Figure 2:
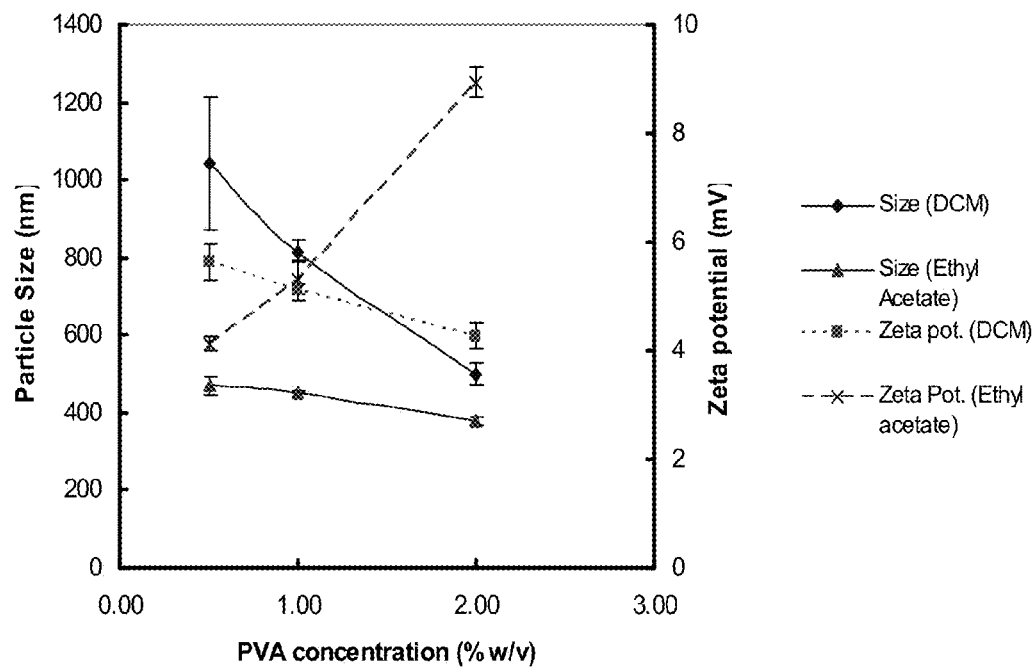
FIG. 2 is a plot of size and zeta potential vs. PVA concentration for formulations where lactose was used without Surfynol 104 PG-50™ and PEG.

The particle size decreased as we compared with formulations without addition of lactose, regardless of the type of organic solvent used. The decay was much more pronounced in case of DCM as illustrated by results presented in FIG. 2: the z-average size of particles dropped from more than 1200 nm to 450 nm, when lactose was added to the formulation.

Zeta potentials were in the positive range because of the presence of chitosan in the formulation. Its initial concentration was varied between 0.05, 0.1 and 0.3% (w/v) and the optimisation of the formulation was done with chitosan 0.3%, which resulted in a high positive zeta potential ~+45 mV.

3.2.2 Effect of Surfynol 104 PG-50™ on Particle Size and Yield

Nonionic surfactants, based on acetylenic diol chemistry, represent a unique class of surfactants providing low surface tension and good de-foaming and surface wetting characteristics.

Contrary to most surfactants that orient vertically at the water/air interface, the acetylenic diol surfactants orient horizontally due to their molecular structure. A compact molecule of this surfactant can migrate very rapidly to the interfacial region providing low values of the dynamic surface tension (DST). It was reported that for a Surfynol 104 PG-50™ bulk concentration of $2.10^{-6}$ $mol \cdot cm^{-3}$, the DST dropped around 35 $dynes \cdot cm^{-1}$. It is, indeed, this specific property of significantly decreasing the surface tension which motivated us to select it as a co-surfactant in our formulations.

Surfynol 104 PG-50™ was added to the internal oil phase before introduction of the drug aqueous phase. The product obtained was characterised by a very small particle size about 230 nm and the experimental results were reproducible.

The size distribution was equally very narrow (PolyDispersity Index (PDI) ~0.1) due presumably to the capability of Surfynol 104 PG-50™ to prevent aggregation.

3.2.3 Effect of PEG and Stearic Acid on Morphology

It is well established that polyethylene glycol (PEG) is extensively used in drug delivery strategies in order to generate entities which are less easily recognised by macrophages and hence exhibit prolonged circulation times in the blood. On the biological level, coating nanoparticles with PEG sterically hinders interactions of blood components with their surface and reduces the binding of plasma proteins with PEGylated nanoparticles. This prevents drug carrier interaction with opsonins and slows down their capture by the reticulo-endothelial systems (RES).

Figure 3:
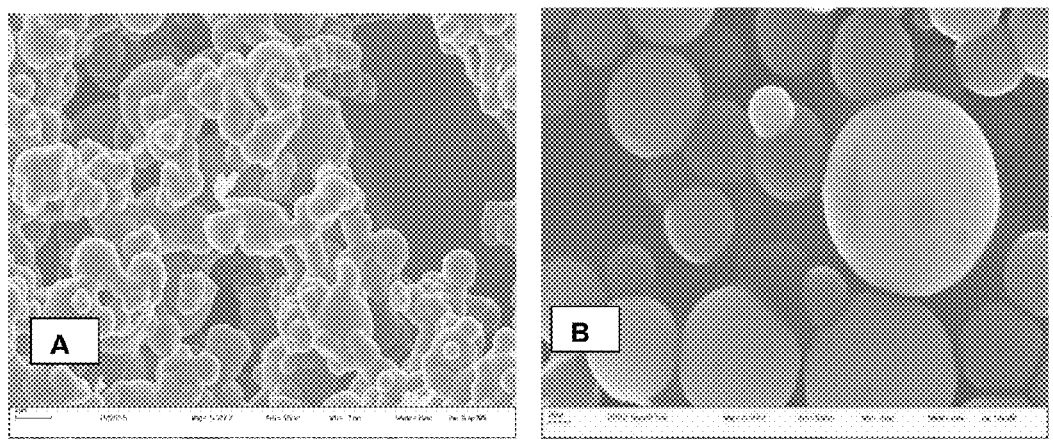
FIGS. 3A and 3B are SEM photos of spray dried INH-loaded PLGA nanoparticles: A. Formulation without stearic acid and PEG and B. formulation with stearic acid and PEG (Measuring bars represent both 200 nm).

PEG was introduced together with PVA in the external phase at an initial concentration of 0.5% w/v, dissolved in de-ionised water As we combine the presence of 5 ml of PEG (0.5% w/v) in aqueous external phase and 2 ml of stearic acid (0.2% w/v) added into the oily phase of the polymer, as a co-surfactant together with Surfynol 104 PG-50™, a significant improvement of the surface morphology was observed, as depicted in FIG. 3. The reading on Zetasizer provided smaller particles size of about 270 nm with a very narrow distribution (PDI ~0.2).

4. Examples of the Use of Gemini Surfactants in the Invention

This first example below relates to the preparation of PLGA nanoparticles loaded with isoniazid in accordance with our inventive process whereby a water-in-oil-in water (w/o/w) double emulsion is fed into a two-fluid nozzle and spray dried through a bench top spray dryer Buchi B290. Briefly, multifunctional polymeric nanocarriers were produced by first dissolving the drug into an aqueous phase whereas, the polymeric carrier material was dissolved in an organic phase of ethyl acetate, to which stearic acid and a drop of Dynol™ 604 surfactant or Dynol™ 607 surfactant (Air Products and Chemicals, Inc) was also added. Dynol™ 604 and Dynol™ 607 surfactants are both a ethoxylated molecules of 2,5,8,11-tetramethyl-6-dodecyn-5,8-diol with 4 or 7 moles of ethylene oxide molecules, respectively. The two immiscible phases were thereafter mixed together by using a Silverson high speed homogeniser. The first water-in-oil emulsion produced was subsequently poured into an aqueous phase of a polymeric stabiliser namely partially hydrolysed (87%) polyvinyl alcohol. At this stage, adjuvants comprising lactose, partially de-acetylated chitosan and polyethylene glycol were included in the stabiliser solution. After homogenisation by means of a Silverson high speed homogeniser, a relatively stable water-in-oil-in water double emulsion was produced. The double emulsion obtained was immediately fed, by means of a peristaltic pump, into the two-fluid nozzle of a bench top Buchi B290 spray dryer to produce free flowing powder of nanocarriers. The emulsion was dried between 90 and 100° C. and the atomising pressure was varied between 5 and 7 bars.

The powder was thereafter characterised using a Zetasizer Nano ZS (Malvern Instruments Ltd, UK). As depicted in Table 2, nanoparticles were produced that featured very small particle size and a positive surface charge. When a hydrophobic drug (i.e. rifampicin) was used, we observed a slight increase in particle size but zeta potential values were comparable to the one obtained for isoniazid-loaded PLGA nanoparticles. Table 3 shows characteristics of RIF-loaded PLGA nanoparticles prepared with either Dynol™ 604 or Dynol™ 607 surfactants.

TABLE 2

INH-loaded PLGA nanoparticles prepared with different types of Gemini surfactants

|  | Size (nm) | PDI | Zeta potential (mV) |
|---|---|---|---|
| Dynol ™ 604 | 277.0 | 0.2 | 14.2 |
| Dynol ™ 607 | 304.6 | 0.3 | 9.7 |

TABLE 3

RIF-loaded PLGA nanoparticles prepared with different types of Gemini surfactants

|  | Size (nm) | PDI | Zeta potential (mV) |
|---|---|---|---|
| Dynol ™ 604 | 352.6 | 0.3 | 11.8 |
| Dynol ™ 607 | 388.3 | 0.3 | 9.5 |

As additional examples, the following non-ionic/anionic Gemini surfactants (i.e. Surfynol 485, Surfynol FS-85 and Surfynol OP-340) obtained from Air Products and Chemicals Inc., were also used in the organic phase of the first emulsion. Particles with similar results were obtained as depicted in Table 4.

TABLE 4

INH-loaded PLGA nanoparticles prepared with different types of Gemini surfactants

|  | Size (nm) | PDI | Zeta potential (mV) |
|---|---|---|---|
| Surfynol 485 | 242.0 | 0.2 | 12.7 |
| Surfynol FS 85 | 296.0 | 0.3 | 33.7 |
| Surfynol OP 340 | 480.5 | 0.4 | 45.4 |

As regards the last set of non-ionic/anionic surfactants (Surfynol FS 85 and Surfynol OP 340), their addition into the formulations resulted in nanoparticles with an increased positive surface charge and a yield of recovery from the spray dryer around 90% per solid weight was obtained.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

The invention claimed is:

1. A process for the production of nanoparticles for drug delivery, said nanoparticles being produced by:
   preparing a double emulsion of water-oil-water including one or more polymers which form the basis of the nanoparticles;
   blending the drug to be delivered into one of the emulsion phases;
   doping either the oil-phase or the outer water-phase with a carbohydrate;
   doping the oil-phase, the outer water-phase, the internal water-phase, or both water phases with a surfactant; and
   spray drying the drug-containing water-oil-water double emulsion having doped emulsion phases to remove both the oil-phase and the water-phases simultaneously, thereby forming nanoparticles having a particle size distribution of 100 nm to 1000 nm.

2. The process of claim 1, wherein the carbohydrate is a saccharide.

3. The process of claim 2, wherein the saccharide is a disaccharide.

4. The process of claim 3, wherein the disaccharide is selected from the group consisting of lactose, maltose, isomaltose, mannobiose, trehalose, and cellobiose.

5. The process of claim 2, wherein the saccharide is combined with a cationic biodegradable muco-adhesive polysaccharide.

6. The process of claim 5, wherein the polysaccharide is chitosan.

7. The process of claim 1, wherein the surfactant is a Gemini surfactant.

8. The process of claim 1, wherein the surfactant is a non-ionic surfactant.

9. The process of claim 1, wherein the surfactant is a polymeric non-ionic surfactant.

10. The process of claim 9, wherein the polymeric non-ionic surfactant in the outer water-phase is partially hydrolysed polyvinyl alcohol.

11. The process of claim 1, wherein there is a polymer in the oil-phase of the emulsion.

12. The process of claim 11, wherein the polymer in the oil-phase is poly(lactic-co-glycolic acid).

13. The process of claim 1, wherein the one or more polymers are present in both the oil-phase and the outer water-phase.

14. The process of claim 1, wherein the drug is added to the oil-phase.

15. The process of claim 1, wherein the drug is a hydrophilic drug and is added to the internal water-phase.

16. The process of claim 14, wherein the drug is hydrophobic.

17. The process of claim 1, wherein the drug is Rifampicin, Isoniazid, Ethambutol, or Pyrazynamide.

18. The process of claim 1, wherein the outer water-phase of the emulsion includes polyethylene glycol.

19. The process of claim 1, wherein the oil-phase includes stearic acid.

20. The process of claim 1, wherein the nanoparticles thus formed are spherical.

21. The process of claim 20, wherein the particle size distribution of the nanoparticles is from 180 nm to 250 nm diameter.

22. The process of claim 1, wherein the one or more polymers are present in both the oil-phase and the internal water-phase.

* * * * *